United States Patent
Amir et al.

(10) Patent No.: US 8,534,144 B2
(45) Date of Patent: Sep. 17, 2013

(54) APPARATUS AND METHOD FOR DETERMINING THE INTERNAL CLEANLINESS OF A TUBE

(75) Inventors: Noam Amir, Ness-Ziona (IL); Tal Pechter, Ramat-Hasharon (IL)

(73) Assignee: AcousticEye Ltd, Tel Aviv (IL)

( * ) Notice: Subject to any disclaimer, the term of this patent is extended or adjusted under 35 U.S.C. 154(b) by 349 days.

(21) Appl. No.: 12/939,455

(22) Filed: Nov. 4, 2010

(65) Prior Publication Data

US 2011/0112776 A1 May 12, 2011

Related U.S. Application Data

(63) Continuation-in-part of application No. 11/996,503, filed as application No. PCT/IL2006/000860 on Jul. 25, 2006, now abandoned.

(60) Provisional application No. 60/703,450, filed on Jul. 29, 2005, provisional application No. 61/257,869, filed on Nov. 4, 2009.

(51) Int. Cl.
*G01G 9/00* (2006.01)

(52) U.S. Cl.
USPC .............................. 73/865; 73/609

(58) Field of Classification Search
USPC ............ 73/865, 37, 609, 618, 620, 622, 627, 73/628; 702/56; 134/1, 113, 227
See application file for complete search history.

(56) References Cited

U.S. PATENT DOCUMENTS

| | | | | |
|---|---|---|---|---|
| 4,966,177 A * | 10/1990 | John et al. | ......................... | 134/61 |
| 5,793,833 A * | 8/1998 | Imai | ................................ | 377/10 |
| 6,290,778 B1 * | 9/2001 | Zugibe | ............................. | 134/1 |
| 6,325,025 B1 * | 12/2001 | Perrone | ......................... | 122/379 |
| 6,339,959 B1 * | 1/2002 | Natapov | .......................... | 73/239 |
| 6,470,749 B1 * | 10/2002 | Han et al. | ......................... | 73/622 |
| 6,572,709 B1 * | 6/2003 | Kaneda et al. | .................... | 134/1 |
| 7,164,476 B2 * | 1/2007 | Shima et al. | ............... | 356/241.1 |
| 7,542,539 B2 * | 6/2009 | Frattini et al. | ................ | 376/308 |
| 7,673,525 B2 * | 3/2010 | Huang | ...................... | 73/861.25 |
| 7,890,197 B2 * | 2/2011 | Francino et al. | ................ | 700/30 |
| 8,246,751 B2 * | 8/2012 | Zhang et al. | ...................... | 134/1 |
| 2012/0125558 A1 * | 5/2012 | Nortman et al. | ............. | 165/11.1 |

* cited by examiner

*Primary Examiner* — J M Saint Surin
(74) *Attorney, Agent, or Firm* — Smith Risley Tempel Santos LLC; Gregory Scott Smith

(57) ABSTRACT

A system to measure the internal state of a bundle of tubes by injecting a signal into each tube of the bundle, receiving reflections from the tube due to anomalies within the tube, then analyzing the reflections to determine the type or characteristics about the anomalies. The analyzed information is stored in database to be used for statistical processing. Further, the device can be used in the performance of a cleaning process by conducting an initial assessment of the tubes in a bundle of tubes, comparing the stored data and estimating the number of cleaning cycles that will be required, and re-conducting the evaluation of the state of the tubes after every cleaning cycle or after every few cleaning cycles.

23 Claims, 6 Drawing Sheets

APPARATUS AND METHOD FOR DETERMINING THE INTERNAL CLEANLINESS OF A TUBE

CROSS-REFERENCE TO RELATED APPLICATIONS

This application is a non-provisional application being filed under 35 USC 111 and 37 CFR 1.53(b) and claims the benefit under 35 USC 119(e) of the prior filing date of the U.S. Provisional Application for patent that was filed on Nov. 4, 2009 and assigned Ser. No. 61/257,869, which provisional is hereby incorporated by reference in its entirety. This non-provisional application is also is filed as a continuation-in-part of the U.S. national patent application that was filed on Jan. 23, 2008 and assigned Ser. No. 11/996,503 now abandoned, which application claims priority to the PCT application PCT/IL06/000860 that filed on Jul. 25, 2006, and which further claims priority to the U.S. provisional application that was filed on Jul. 29, 2005 and assigned Ser. No. 60/703,450, which applications are herein incorporated by reference in their entirety.

BACKGROUND

There is a variety of applications that utilize tubes, or a bundle of tubes for delivering or extracting liquid, gas, etc. A few non-limiting examples of such applications are seen in systems such as typical plumbing environments, large-scale plumbing environments, heat exchangers, reactors, boiler systems, etc. More particularly, one can typically observe the use of heat exchangers in systems such as power stations, refineries, chemical plants, air conditioning systems, etc. In applications that employ the use of such tubing for the transfer of liquid, the fluid flowing through the tubes may result in the facilitation of an accumulation of deposits on the inner surface of the tubes. The accumulation of such deposits results in degrading the efficiency of the tube and/or bundle of tubes. The accumulation in such environments may depend on a variety of circumstances, such as the ambient temperature of operation, the contents of the liquid, the flow rate, the flow volume, the type of material used in fabricating the tubes, the shape of the tubes (straight or bent), the size of the inner diameter, etc. As such, the accumulation of deposits on the inner surface of the tube(s) can occur at a variety of rates ranging from gradual to rapid accumulation. The accumulation of the deposits within the interior of the tube and/or tubes can have an adverse effect on the operation of the system utilizing the tubes. For instance, the accumulation may result in the reduction of heat transfer, reduction in the ability to cool a system or simply an obstruction of flow. Therefore, it is common practice in the maintenance of such systems to clean out the tubes periodically. The cleaning process is complicated by the fact that some deposits, for example scale, can be very hard to remove. To successfully clean and maintain the tubes, the cleaning process often involves several cleaning stages for the successive removal of such deposits.

Measuring the effectiveness of the cleaning process at the end of each stage and/or at the conclusion of the process is a difficult task. There are a few known methods for evaluating the cleaning. The most common method is to examine the tubes visually using a borescope. However, using a borescope in a bundle of tubes is very time consuming. In addition the borescope can only be used in the examination of straight tubes. Furthermore, the results of the evaluation using a borescope are objective and depend greatly upon the capabilities, judgment, opinions and the current condition of the user conducting the evaluation.

It should also be appreciated by those of ordinary skill in the art that the methods utilized in the current state of the art—suffer from several deficiencies, such as but not limited to, the amount of time required in performing the evaluation, the dependency on the operator, the limitation of not being used in bundles of curved tubes, etc.

BRIEF SUMMARY

There is a need in the art for a technique and/or system and/or method that can measure or evaluate the cleanliness or clearness of a large number of tubes, such as a bundle of tubes, in a timely manner. Furthermore, there is a need in the art for a technique and/or system and/or method that can perform an evaluation of tubes objectively and automatically, independent of the capabilities and judgments of the user or operator. There is also a need for a technique and/or system and/or method that can evaluate the cleanliness or clearness of bent, curved and spiraled tubes.

The above-described deficiencies do not limit the scope of the inventive concepts of the present disclosure in any manner. The deficiencies are presented for illustration only.

Several exemplary embodiments of a measurement apparatus, that performs a quality control analysis of the remedial process, which may include a cleaning process, purging process, resurfacing process, etc., are described. An exemplary embodiment first applied before the remedial process commences in order to assess the initial condition of the tubes. It is then applied successively after each stage of cleaning to assess the effectiveness of each act of the cleaning process, showing the present condition of the tubes and giving indications whether additional cleaning phases are necessary.

More particularly, one embodiment of the measuring device or system that can be used in the above-described cleaning process is used to evaluate the interior state of one or a plurality of tubes, such as in a bundle of tubes. The system includes a processing unit or some processing capability or control capability (collectively referred to as a processing unit). The processing unit interfaces to a signal injector and a signal detector. The signal detector includes an interface tube, which is an element that can be coupled or interfaced to a tube to be tested. The signal injector operates to create a wave in the tube. The wave can be an acoustic wave for example. In other embodiment the wave can be electro-magnetic waves or other signal types. The wave then propagates into the target tube, the tube under test. As the wave encounters—constrictions within the interior of the tube, such as deposits, accumulations, fractures, pits, etc., the wave or portions thereof is reflected. The reflected waves propagate back up the tube where a sensor, such as a pressure sensor, transducer, etc., detects a signal, which was created from the received reflected waves. The detected signal, or information about the reflected wave, is then provided to the processing unit which can then evaluate the information to identify what, if any, anomalies are present in the tube.

In conducting the evaluation, the processing unit operates to identify statistical information concerning the anomalies in each target tube including statistics such as the number of blockages, number of cleaning cycles required to restore tube interior to a desired status or a threshold state of cleanliness, the number of faults in the tube, the percentage of blockage, etc.

DETAILED DESCRIPTION OF EMBODIMENTS OF THE INVENTION

The disclosure describes various embodiments, as well as features, aspects functions, etc. of such embodiments of a tube testing device. Various embodiments of the tube testing device are based on the use of Acoustic Pulse Reflectometry (APR).

Now turning to the figures, the various embodiments, as well as features, aspects and functions that may be incorporated into the various embodiments are described in more detail.

Figure 1:
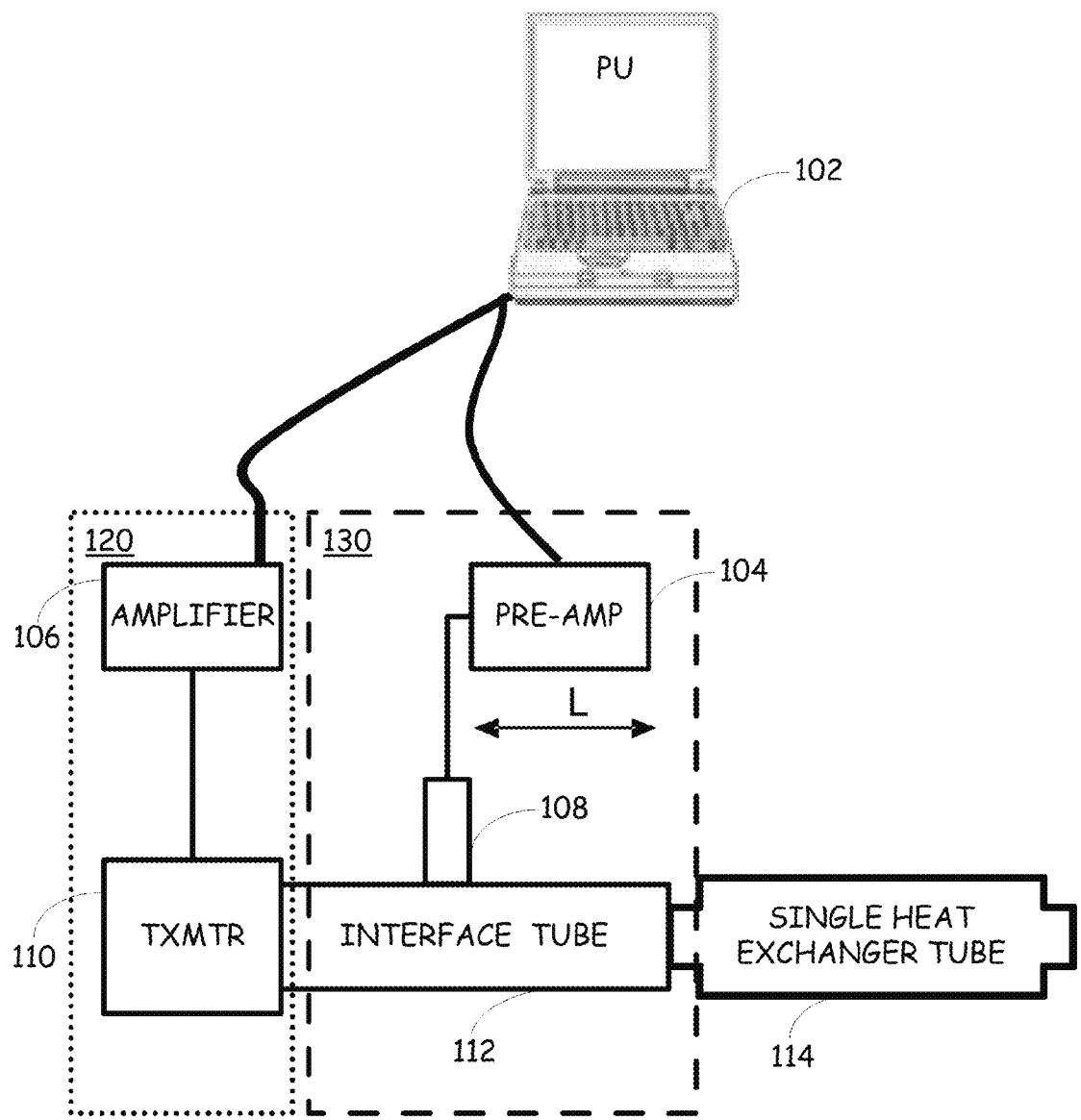
FIG. 1 is a block diagram illustrating relevant elements of an exemplary embodiment of a system for measuring and evaluating the cleanliness of a plurality of tubes.

FIG. 1 is a block diagram illustrating relevant elements of an exemplary embodiment of a system for measuring and evaluating the cleanliness of a plurality of tubes. The illustrated hardware components of the exemplary measuring system are configured to provide Non Destructive Testing (NDT). It should be noted that the configuration illustrated in FIG. 1 is used for illustration purposes only and therefore is not in shown to any particular scale and the illustrated functional boundaries are not absolutely necessary in the actual implementation of the measuring system. For example, the length of the interface tube 112 can be shorter, longer or the same as the length of the exchanger tube 114.

The illustrated embodiment includes a signal injector 120 and a signal detector 130. It should be understood that the term signal and wave is used interchangeably in this description and encompasses any form of energy that can be propagated through the tube and reflected and detected. The signal injector 120 is configured to inject a signal into a medium, or interface tube 112, which acts as an interface to the target tubes being tested 114. The signal detector 130 includes a sensor that detects signal reflected back from the target tubes 114 into the interface tube 112. The signal injector 120 and signal detector 130 may operate as a stand-alone unit, a stand-alone unit that interfaces and/or reports information to other system, a support unit that is controlled by an external processing unit 102, as well as other structures and/or configurations. For instance, in the stand-alone configuration, the processing unit may be incorporated into the signal injector and/or the signal detector 130. In such embodiments, the processing unit 102 may be as simple as a microcontroller, an ASIC or even simply analog and/or digital control circuitry. The stand-alone unit may include a user interface for initiating a test sequence or, it may simply be activated by coupling the interface tube 112 to a tube under test 114. The recorded signal may be stored in internal memory and/or information regarding the detection may be displayed to a user in a variety of manners including the use of an LCD or even simple codes displayed using lights or numbers, or audible sounds such as error codes or certain tones or buzzers may also be used.

In the illustrated embodiment, the signal injector 120 is coupled to the processing unit 102 and the tube under test 114. The signal detector 130 is coupled to the processing unit 102 and the tube under test 114.

More specifically, in the illustrated measuring system, the processing unit 102 synthesizes an acoustic pulse which is transmitted through a transmitter 110 via an amplifier 106. Thus, the processing unit 102 may include a signal generator or, a signal generator can be external to the processing unit 102, such as in the signal injector 120 or in-line between the processing unit 102 and the signal injector 120. The signal is converted into an acoustic wave by TXMTR 110, which can be a loudspeaker or similar transducer. The acoustic wave first propagates down an interface tube 112, where it can be detected and/or recorded by a sensor, such as a pressure sensor 108. Sensor 108 may be a transducer, a microphone or any of a variety of other devices that can detect a signal. The acoustic wave can be a pulse of an acoustic wave for example then travels down a tube 114—the target tube that is being examined. In the illustrated embodiment the target tube 114 is shown to be a heat exchanger tube as an example. Any change in cross section of the target tube 114 will cause a reflection that will propagate back up the tube 114 and the interface tube 112, to be recorded by the pressure sensor 108, amplified by a pre-amp 104 and stored in the computer 102. The recorded reflections are analyzed in the computer 102 in order to identify the types and or severity of the faults that caused or resulted in creating the reflections. As non-limiting examples, the faults may be blockages (full or partial), pitting, erosion, cracks, kinks, bulges and holes. It will be appreciated that in some embodiments, multiple interface tubes can be utilized with each having a pressure sensor 108 but being fed by the same transmitter. In such embodiments, multiple tubes can be tested at the same time or in consecutive fashion.

In addition to the measuring process as disclosed above, processing unit 102 can be configured to store measuring results from previous cleaning process including the performance of the bundle of tubes before and after each cleaning cycles. This data can be stored in a memory element (such as within an associated database structure in the memory element) and such memory element can be external or in internal permanent memory of the processing unit 102 itself. The stored data can be used for statistical analysis for determining a current situation of each tube in the buddle and the situation of the bundle as a whole.

The stored information can include parameters to identify the interior state of the tube, such as but not limited to: the cleaning date, the performance of the bundle before a cleaning cycle, the results of measuring the dirt in the bundle before cleaning, dirt values after cleaning and the bundle's performance after cleaning. The performance of a bundle can be defined for example by: the temperature difference of the liquid between the temperature in the ingress of the bundle and the temperature at the egress of the bundle, the pressure differentials between the pressure of the ingress and egress of the bundle; the flow speed; etc. The dirt values can be referred as the parameters regarding the current cleanliness level of the bundle. Exemplary dirt values can be represented in one or more ways, for example: a rate value or roughness value, the number of blockages above a certain amplitude per a meter of a tube or the distribution of peaks in the signal (number and height) per tube or per a group of tubes; an amplitude value:

an average amplitude of a blockage in a pipe, in the bundle; the maximum amplitude of the worse blockage in a tube, which is above a certain level, etc.

Processing unit 102 can be further configured to process the stored data and based on current measurements and the stored data, including the time differences between the cleaning processes of the stored data can determine whether cleaning process is needed or when a next cleaning process needs to be performed, or whether a cleaning can help or if a tube should be replaced or plugged. More information of the operating of processing unit 102 is disclosed below in conjunction with FIG. 5 and FIG. 6.

It will be appreciated that the measuring and evaluating system can advantageously be used in tubes that are not necessarily linear or uniform. For instance, the tubes under test may have bends and may have varying inner diameters. In some embodiments, the processing unit can filter out reflections from known obstructions, such as bends or diameter changes and so to only provide information on blockages, cracks or other anomalies. In other embodiments, the processing unit can employ signal processing capabilities to identify and differentiate between reflections from tube bends and/or diameter changes from other anomalies. In yet other embodiments, reflection signatures can be taken and recorded for new tubes that are known to be free from anomalies and these stored signal signatures can then be used to filter out subsequent signal recordings of tubes under test. It will also be appreciated that different types, patterns, frequencies, etc. of signals can be used to detect different anomalies. For instance, some deposit materials may be more reflective at certain frequencies than at others and thus, using specific signal frequencies to detect for particular deposits may improve the accuracy of the detection.

Figure 2:
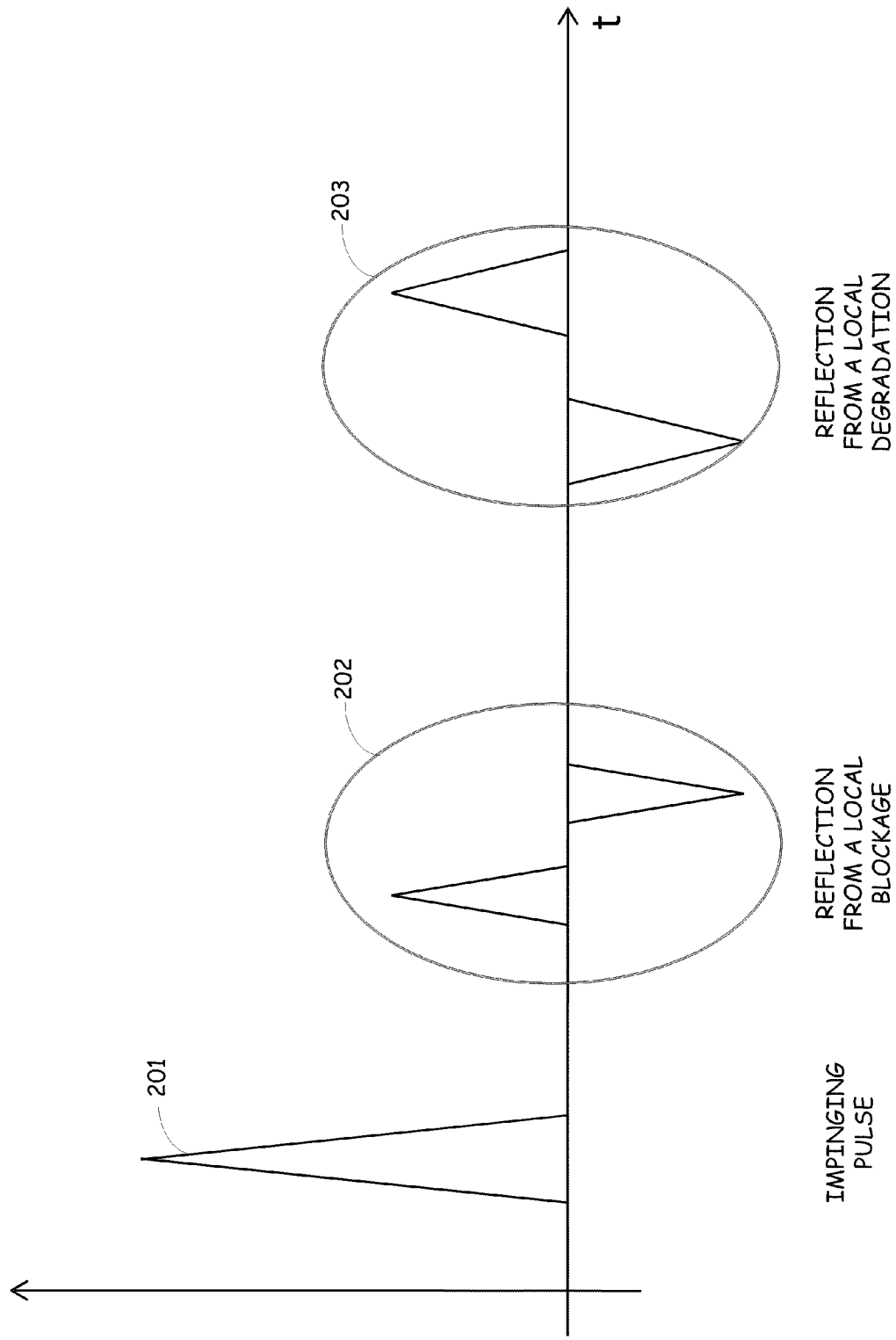
FIG. 2 is a waveform timing diagram that illustrates typical reflections from a local blockage and a local degradation in a target tube.

FIG. 2 is a waveform timing diagram that illustrates typical reflections from a local blockage and a local degradation in a target tube. The reflections illustrated in FIG. 2 are non-limiting examples of the reflections from different faults in an exemplary target pipe. Supposing the impinging acoustic pulse 201 to be a sharp positive pulse as depicted in FIG. 2, the reflection from a local blockage will appear as a positive pulse (reflected from the leading edge of the blockage) followed by a negative pulse (reflected from the terminating edge of the blockage) as depicted as element 202. A reflection from wall loss such as pitting or erosion will be a negative pulse (reflected from the leading edge of the wall loss) followed by a positive one (reflected from the terminating edge of the wall loss) as depicted in element 203. More information on an exemplary NDT application and the faults is described in U.S. patent application Ser. No. 11/996,503, the content of which incorporated herein by reference.

After observing a plurality of tubes before and after cleaning, it has been discovered that there are differences between the reflection coming from clean tubes and unclean tubes. More specifically, it was determined that tubes that have been cleaned prior to an NDT inspection will have isolated identifiable faults such as those presented in FIG. 2. Dirty tubes, on the other hand, have densely spaced fouling and deposits which are in effect, multiple closely spaced blockages. Upon presentment of an impinging pulse in such an environment, this results in multiple closely spaced peaks in the signal recorded by pressure sensor 108 (FIG. 1). Removal of the deposits from the tube during the cleaning process will result in the reflected signals having lower peaks, as the deposits become smaller. The differences are demonstrated in FIG. 3 and FIG. 4.

Figure 3:
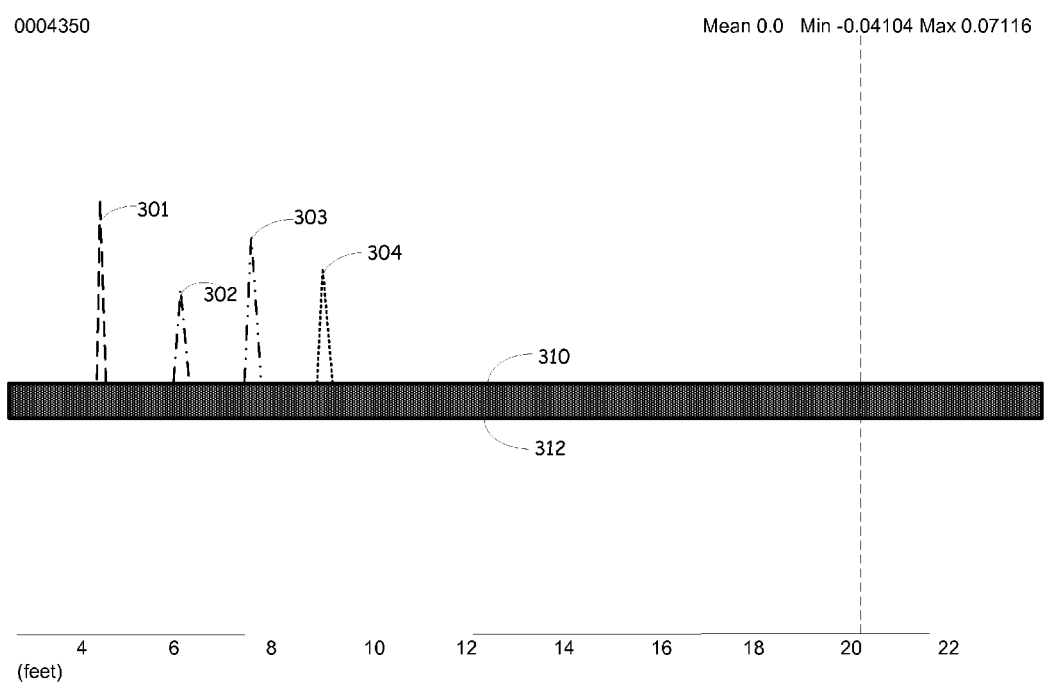
FIG. 3 is a signal diagram illustrating overlaid traces of measurements from several exemplary dirty target tubes.

FIG. 3 is a signal diagram illustrating overlaid traces of measurements from several exemplary dirty tubes. Upon examination of FIG. 3, it is clear that there are prominent peaks (such as peak 301, 302, 303 and 304) indicating several large blockages, and an overall noisiness shown as existing between levels 310 and 312 corresponding to rough internal surface of the tubes, due to deposits.

Figure 4:
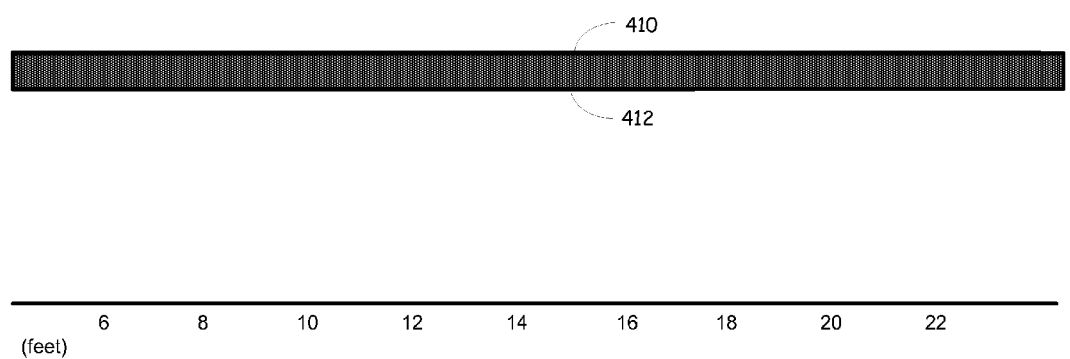
FIG. 4 is a signal diagram illustrating overlaid traces of signals corresponding to internal surface of the target tubes after cleaning.

FIG. 4 is a signal diagram illustrating overlaid traces of signals corresponding to internal surface of the target tubes after cleaning. Measurements taken from the same group of target tubes after cleaning are illustrated in FIG. 4. As is clearly shown in FIG. 4, the signals reside between lines 410 and 412 and are much more uniform, and smoother thus corresponding with a smoother internal surface of the target tubes.

Figure 5:
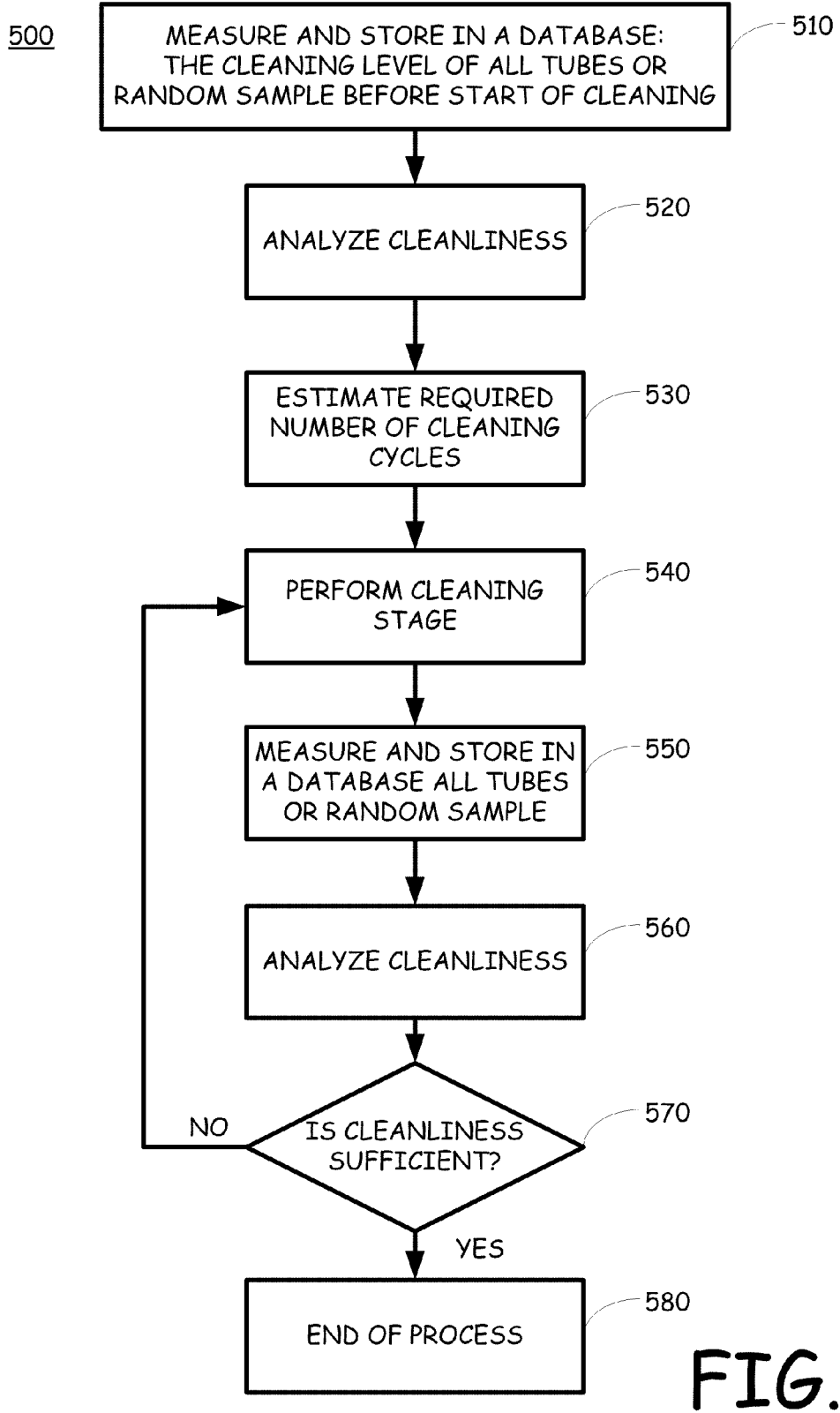
FIG. 5 is a flow diagram illustrating relevant acts of an exemplary method for analyzing and evaluating the effectiveness of a cleaning process.

FIG. 5 is a flow diagram illustrating relevant acts of an exemplary method for analyzing and evaluating the effectiveness of a cleaning process. Within an environment of a heat exchanger, the exemplary method 500 can take measurements over a large number of tubes and then perform a statistical analysis of these measurements in order to present the user with an overall picture of the condition of the heat exchanger being examined. Further, the information is stored in a database or permanent memory and be used as statistical data for future cleaning processes. In some embodiments the bundle performance before and after cleaning can be taken too and be used for analyzing the dirt situation in the bundle. This overall picture can provide the user with metrics regarding the likelihood of the occurrence of a breakdown on a per tube basis, groups of tubes, or the entire heat exchanger. Non-limiting examples of some of the statistics that can be determined include, but are not limited to the following list: average number of blockages, in a tube and/or in the bundle, above a certain threshold, worse blockage per tube, measures of roughness compiled from the distribution of peaks in the signal (number and height) per tube or per a group of tubes, an average number of cleaning that is required in order to reach a required level of cleanness of tubes in a certain condition, etc. Generally, the causes of dirt in the tubes may vary according to many factors including, but not necessarily limited to, the types of tubes and the environments in which the tubes are operating. The contamination can be caused by sludge, scaling, marine organisms, corrosion etc. The number of cleaning cycles required to reduce deposits or accumulations in a tube to acceptable levels depends strongly on the type of the deposits, and therefore also varies. Thus, a cumulative knowledge base built into the system and incorporating the results from all or a large number of the previous sessions can be used as the accumulated information (i.e., tube type, operating environment, number of actual cleaning cycles) to give an estimate of the number of cleaning cycles required to achieve a requested or target degree of cleanliness.

The exemplary APR system that is illustrated in FIG. 1 can be used in conjunction with the acts of method 500 to measure and store in a database a random sample of tubes or all the tubes in a bundle of tubes prior to cleaning 510. In some exemplary embodiments act 510 further includes measuring and storing the bundle performance before the cleaning. The system conducts an analysis of the cleanliness (the level of dirt in the bundle of tubes) of the measured sample of tubes compares it to information stored in the database and then reports on the level of cleanliness 520. In the exemplary embodiments in which the performance of the bundle is measured and stored, those parameters are also processed in addition to the cleanliness level. The level of cleanliness (the dirt values) can be expressed by the average number of blockages above a certain threshold in a tube from the plurality of tubes, worse blockage per tube, measures of roughness compiled from the distribution of peaks in the signal (number and height) per tube or per a group of tubes, etc. The performance values can be expressed by the temperature difference of the liquid between the temperature in the ingress of the bundle and the temperature at the egress of the bundle, the pressure falls between the pressure of the ingress and egress of the bundle; the flow speed; etc.

Based on past similar cases available to the system or stored within its knowledge base, the system estimates the number of cleaning cycles required to bring the tubes to an accepted level of cleanliness 530. The system can then enter a loop that includes the performance of a cleaning stage 540 followed by the process of measuring all or a random sample of the tubes 550 and then again, analyzing the cleanliness of the tubes 560 based on the most recent cleaning stage. In some embodiments act 550 may further include measuring and storing the bundle performance after the cleaning.

In some embodiments, the knowledge base can be stored in database and after each cleaning stage or session, the database can be updated with the new results. The database can be organized and structured in a variety of ways, for instance, the entries may be divided according to the type of tubes, the application of the bundle, etc. After each cleaning cycle, the system determines if 570 the cleanliness level of the tubes has met the target requirements. In some embodiments the decision can be based also on the performance measurement of the bundle of tubes, yet in other embodiment, the decision can be based on both: the level of dirt (or cleanliness level) and the performance o the bundle. If not, this process is repeated by returning to the act of performing a cleaning stage 540. In some embodiments, if after several cleaning process the bundle performance and/or the level of dirt are not improved then method 500 may recommend to replace one or more tubes or the entire bundle.

However, if 570 the cleanliness level of the tubes has met the target requirement, the process stores the date and the number of cleaning cycles in the database to be used for future cleaning processes and generates and produces a detailed report. In some embodiments, the report shows quantitative measures described above for the initial, interim and final conditions of the tubes.

The system can also be used to determine the rate of debris accumulation. For instance, if measurements are taken and stored on a periodic basis following a cleaning, then data can be accumulated regarding how long it takes, following a cleaning cycle, for the debris to accumulate to a threshold level. After accumulating this data over a period of time, the system can then accurately estimate when the next cleaning cycle is due.

Some exemplary embodiments of an evaluation system can be configured to collect information regarding the overall geometry or structure of the tubing in the bundle. In such embodiments, reflections of signals caused by bends, compressions, joints, etc., are expected to the system and can be filtered out as not being caused by accumulations within the tubes.

The various embodiment of the measuring device can be implemented as a stand-alone apparatus, or integrated with cleaning equipment or a cleaning system. Further, the measuring device—could be implemented as a tool for testing one tube at a time, or together with a robotic manipulator as a system for automatically testing a large number of tubes.

Some exemplary embodiments may include a centralized updating center. Such a center can include a server that can be loaded from time to time with the results generated by a plurality of users regarding the history of their cleaning sessions. Based on the enlarged collected data, the server can perform statistical analyses in order to determine the required number of cleaning cycles needed to clean a bundle of tubes. The updated formulations can be loaded back to the users' equipment.

Figure 6:
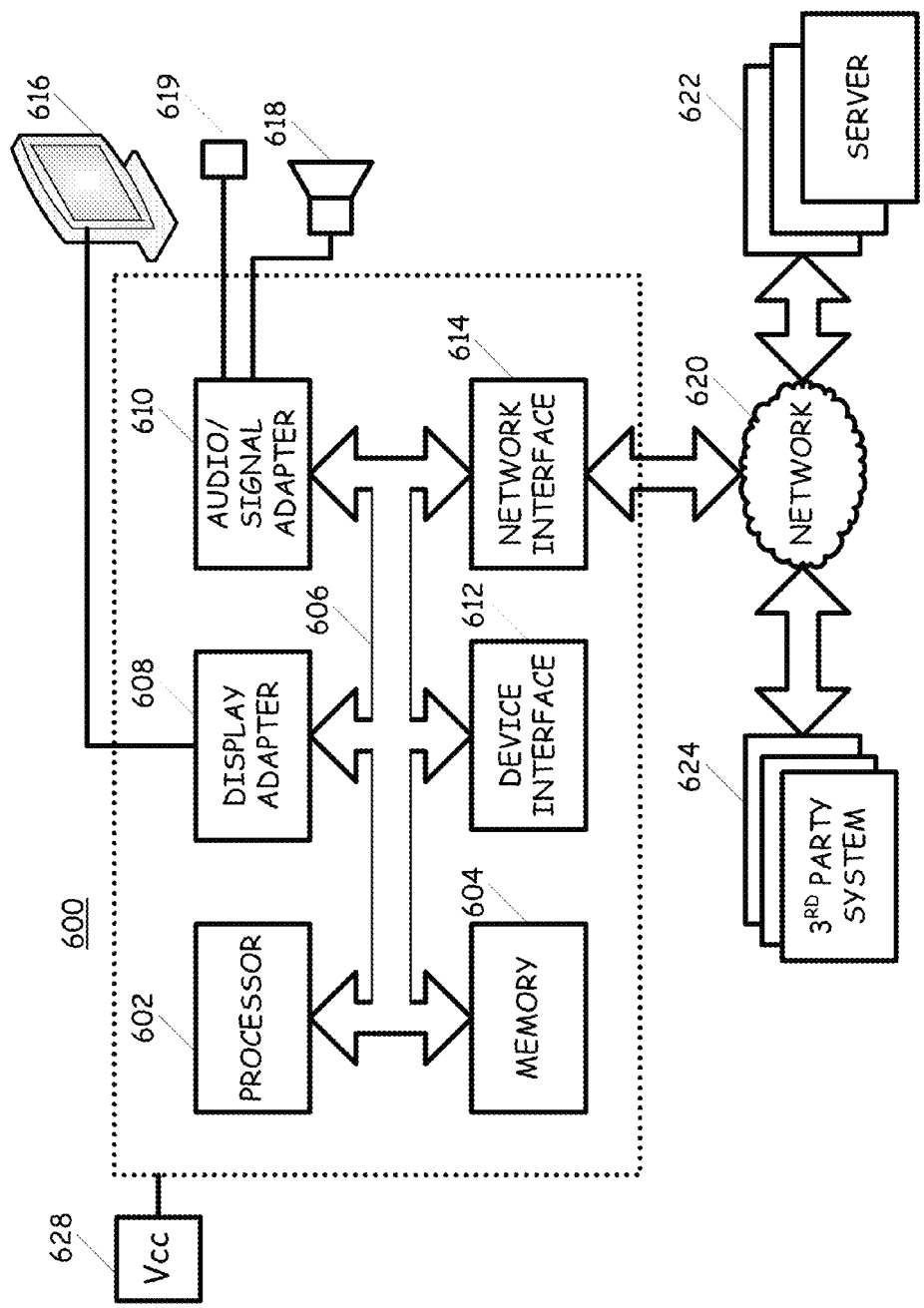
FIG. 6 is a functional block diagram of the components of an exemplary embodiment of the measuring system, as well as other embodiments thereof.

FIG. 6 is a functional block diagram of the components of an exemplary embodiment of the measuring system, as well as other embodiments thereof. It will be appreciated that not all of the components illustrated in FIG. 6 are required in all embodiments of the measuring device but, each of the components are presented and described in conjunction with FIG. 6 to provide a complete and overall understanding of the components. Further, many specific elements are not presented in FIG. 6 but rather functions and/or functional interfaces are used in a generic fashion to indicate that various embodiments may use a variety of specific components or elements. The measuring system can include a general computing platform 600 illustrated as including a processor 602 and a memory device 604 that may be integrated with each other (such as a microcontroller) or, communicatively connected over a bus or similar interface 606. The processor 602 can be a variety of processor types including microprocessors, micro-controllers, programmable arrays, custom IC's etc. and may also include single or multiple processors with or without accelerators or the like. The memory element of 604 may include a variety of structures, including but not limited to RAM, ROM, magnetic media, optical media, bubble memory, FLASH memory, EPROM, EEPROM, internal or external-associated databases, etc. The processor 604, or other components may also provide components such as a real-time clock, analog to digital converters, digital to analog converters, etc. The processor 602 also interfaces to a variety of elements including a control or device interface 612, a display adapter 608, audio/signal adapter 610 and network/device interface 614. The control or device interface 612 provides an interface to external controls or devices, such as sensor, actuators, transducers or the like. The device interface 612 may also interface to a variety of devices (not shown) such as a keyboard, a mouse, a pin pad, and audio activate device, a PS3 or other game controller, as well as a variety of the many other available input and output devices or, another computer or processing device. The device interface may also include or incorporate devices such as sensors, controllers, converters, etc. For instance, the amplifier 106, the transmitter 110, the preamp 104 and the sensor 108 illustrated in FIG. 1 could all be included in the device interface 612 either as internal or integrated components or, the device interface 612 may interface to the devices as external components. Alternatively the -processing unit 102 illustrated in FIG. 1 could interface to the measuring elements as a stand-alone third party system through control lines, a wired network or a wireless network. The display adapter 608 can be used to drive a variety of alert elements and/or display devices, such as display devices including an LED display, LCD display, one or more LEDs or other display devices 616. The audio/signal adapter 610 interfaces to and drives another alert element 618, such as a speaker or speaker system, buzzer, bell, etc. In the various embodiments of the measuring device, the audio/signal adapter could be used to generate the acoustic wave from speaker element 618 and detect the received signals at microphone 619. The amplifiers, digital-to-analog and analog-to-digital converters may be included in the processor 602, the audio/signal adapter 610 or other components within the computing platform 600 or external there to. The network/device interface 614 can also be used to interface the computing platform 600 to other devices through a network 620. The network may be a local network, a wide area network, wireless network, a global network such as the Internet, or any of a variety of other configurations including hybrids, etc.

The network/device interface 614 may be a wired interface or a wireless interface. The computing platform 600 is shown as interfacing to a server 622 and a third party system 624 through the network 620. A battery or power source 628 provides power for the computing platform 140.

In the description and claims of the present application, each of the verbs, "comprise" "include" and "have", and conjugates thereof, are used to indicate that the object or objects of the verb are not necessarily a complete listing of members, components, elements, or parts of the subject or subjects of the verb.

Various aspects and embodiments of the invention have been described are provided by way of example and are not intended to limit the scope of the invention. The described embodiments comprise different features, not all of which are required in all embodiments. Some embodiments utilize only some of the features or possible combinations of the features. Variations of embodiments described and embodiments comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A system for evaluating the interior state of one or more tubes in a bundle of tubes, comprising:
   a processing unit;
   a memory element communicatively coupled to the processing unit;
   a signal injector interfacing with the processing unit;
   a signal detector interfacing with the processing unit; and
   an interface tube that is coupled to the signal injector and the signal detector and is configured to interface with a current-measured tube of the bundle of tubes under test;
   wherein the processing unit is configured to at least partially control the signal injector to cause the injection of a signal into the interior of the current-measured tube of the bundle of tubes through the interface tube;
   wherein the signal detector is configured to detect a signal reflected back out of the current-measured tube through the interface tube and provide information regarding the reflected signal to the processing unit; and
   wherein the processing unit is further configured to:
      process the information regarding the reflected signal received from each one of the plurality of tubes, to deduce one or more parameters regarding the current interior state of the bundle of tubes,
      store the deduced one or more parameters in the memory element,
      collect one or more parameters regarding the current performance of the bundle of tubes and store it in the memory element, and
      compare the collected one or more parameters regarding the performance of the bundle of tubes to previously stored information in order to determine whether a remedial process is necessary.

2. The system of claim 1, wherein the processing unit is further configured to determine the number of remedial cycles required to bring the tube to a desired interior state.

3. The system of claim 1, wherein the one or more parameters regarding the current interior state are statistical information selected from a group consisting of an average roughness value of the tubes in the bundle, the average size of a blockage in the bundle, and the size of the biggest blockage in each of the tubes.

4. The system of claim 1, wherein the one or more parameters regarding the current interior state are selected from a group consisting of temperature difference between the ingress of the bundle and the egress of the bundle, the pressure difference over the bundle; and the flow speed.

5. The system of claim 1, wherein the signal injector includes a transmitter that is configured to transmit an acoustic wave toward the interface tube.

6. The system of claim 1, wherein the bundle of tubes is part of a heat exchanger.

7. A system for evaluating the interior state of one or more tubes in a bundle of tubes, comprising:
   a processing unit;
   a memory element communicatively coupled to the processing unit;
   a signal injector interfacing with the processing unit;
   a signal detector interfacing with the processing unit; and
   an interface tube that is coupled to the signal injector and the signal detector and is configured to interface with a current-measured tube of the bundle of tubes under test;
   wherein the processing unit is configured to at least partially control the signal injector to cause the injection of a signal into the interior of the current-measured tube of the bundle of tubes through the interface tube;
   wherein the signal detector is configured to detect a signal reflected back out of the current-measured tube through the interface tube and provide information regarding the reflected signal to the processing unit; and
   wherein the processing unit is further configured to:
      process the information regarding the reflected signal received from each one of the plurality of tubes,
      deduce one or more parameters regarding the current interior state of the bundle of tubes and to store the deduced one or more parameters in the memory element, and
      compare the deduced one or more parameters regarding the current interior state of the bundle of tubes to previously stored information in order to determine whether a remedial process is necessary.

8. The system of claim 7, wherein the one or more parameters regarding the current interior state are statistical information selected from a group consisting of an average roughness value of the tubes in the bundle, the average size of a blockage in the bundle, and the size of the biggest blockage in each of the tubes.

9. The system of claim 7, wherein the processing unit is further configured to collect one or more parameters regarding the current performance of the bundle of the and store it in the memory element.

10. The system of claim 9, wherein the one or more parameters regarding the current performance are selected from a group consisting of temperature difference between the ingress of the bundle and the egress of the bundle, the pressure difference over the bundle; and the flow speed.

11. The system of claim 7, wherein the processing unit is further configured to determine the number of remedial cycles required to bring the tube to a desired interior state.

12. The system of claim 7, wherein the signal injector includes a transmitter that is configured to transmit an acoustic wave toward the interface tube.

13. The system of claim 7, wherein the one or more parameters regarding the current interior state of the bundle of tubes comprises an average number of blockages in a tube above a certain threshold.

14. The system of claim 7, wherein the bundle of tubes is part of a heat exchanger.

15. A method for evaluating the interior state of a plurality of tubes, the method comprising the action of identifying the interior state of the bundle by conducting the acts of:
- interfacing an interface tube of a measuring device to a target tube, from to plurality of tubes, to be tested;
- injecting a signal into the interface tube such that the signal propagates through the interface tube and into the target tube;
- detecting signal reflections exiting from the target tube back into the interface tube;
- processing the signal reflections from each one of the plurality of tubes, to deduce one or more parameters regarding the current interior state of the bundle of tubes and to store the deduced one or more parameters into a memory element;
- performing the action of identifying the interior state for a set of the tubes in the bundle;
- analyzing the interior states to identify the number of remedial cycles necessary for the tubes in the set to obtain a threshold interior state; and
- reporting the identified number of remedial cycles on the bundle of tubes.

16. A system for evaluating the interior state of a plurality of tubes, the system comprising the components of:
- a processing unit;
- a signal injector, including at least one transmitter, the signal injector interfacing with the processing unit; and
- a signal detector, including at least one sensor, the signal detector interfacing with the processing unit; and
- at least one interface tube, each interface tube is configured to interface to a tube of the plurality of tubes and is associated with at least one of the at least one transmitters and at least one sensor of the at least one sensors;
- wherein the processing unit is configured to at least partially control the signal injector to cause the at least one transmitter associated with the at least one interface tube to inject a signal into the interior of one or more target tubes through the at least one interface tube;
- wherein the signal detector being configured to detect signals reflected back out of the one or more target tubes and into the at least one interface tube, and provide information regarding the reflected signals for each such target tube to the processing unit;
- wherein the processing unit being configured to:
  - process the information regarding the reflected signals to identify one or more parameters regarding the current interior state of the bundle of tubes and store the processed information in a memory device and
  - compare the one or more parameters regarding the current interior state of the bundle of tubes to previously stored information in order to determine whether a remedial process is necessary.

17. The system of claim 16, wherein the one or more parameters regarding the current interior state of the bundle of tubes are statistical information including at least one of the following statistics: number of blockages, number of cleaning cycles required to restore tube interior to a desired status, and percentage of blockage above a certain level.

18. The method of claim 15, wherein signal reflections from clean tubes are a known quantity and such information is used in the action of processing the signal reflections.

19. The method of claim 15, further comprising the actions of:
- after a remedial cycle is completed, repeating the act of performing the action of identifying the interior state for the tube;
- analyzing the interior states to determine if the threshold interior state has been achieved; and
- indicating whether one or more further remedial cycles are needed.

20. The method of claim 19, wherein the set of tubes is a random sample of the tubes in the bundle.

21. The method of claim 19, wherein the set of tubes is all of the tubes in the bundle.

22. The method of claim 19, wherein signal reflections from clean tubes are a known quantity and such information is used in the action of processing the signal reflections.

23. The method of claim 15, wherein the deduced one or more parameters regarding the current interior state of the bundle of tubes are statistical information including at least one of the following statistics: number of blockages, number of cleaning cycles required to restore tube interior to a desired status, and percentage of blockage above a certain level.

* * * * *